United States Patent [19]

Okorodudu

[11] 4,198,305

[45] Apr. 15, 1980

[54] LUBRICANT COMPOSITIONS

[75] Inventor: Abraham O. M. Okorodudu, West Deptford,, N.J.

[73] Assignee: Mobil Oil Corporation, New York, N.Y.

[21] Appl. No.: 915,483

[22] Filed: Jun. 14, 1978

[51] Int. Cl.$^2$ .............................................. C10M 1/38
[52] U.S. Cl. .................. 252/48.6; 560/125; 560/147; 560/150
[58] Field of Search ............... 252/48.6; 560/125, 147, 560/150

[56] References Cited

U.S. PATENT DOCUMENTS

| | | | |
|---|---|---|---|
| 2,318,629 | 5/1943 | Prutton | 252/48.6 X |
| 2,623,066 | 12/1952 | Murphy et al. | 560/147 X |
| 2,637,741 | 5/1953 | Libenson | 560/147 |
| 2,683,119 | 7/1954 | Smith, Jr. et al. | 252/48.6 |
| 2,691,000 | 10/1954 | Elliott | 252/48.6 |
| 3,136,748 | 6/1964 | Miller et al. | 252/48.6 X |
| 3,282,784 | 11/1966 | Gordon et al. | 560/147 X |
| 3,769,315 | 10/1973 | Keener et al. | 560/147 X |

FOREIGN PATENT DOCUMENTS 522491 3/1956 Canada .................................. 252/48.6

*Primary Examiner*—Andrew Metz
*Attorney, Agent, or Firm*—Charles A. Huggett; Raymond W. Barclay; Howard M. Flournoy

[57] ABSTRACT

Polyesters of polysulfideorganocarboxylic acids have improved solubility in lubricant compositions and thereby impart good load-carrying properties to such lubricants when incorporated therein. Oxidized derivatives thereof wherein at least one of the sulfide groups is oxidized to a sulfoxide or a sulfone, also impart good load-carrying characteristics to lubricants containing same.

7 Claims, No Drawings

LUBRICANT COMPOSITIONS

BACKGROUND OF THE INVENTION

1. Field of the Invention

This application is directed to oil-soluble load-carrying additives consisting of polyesters of certain polysulfideorganocarboxylic acids useful in various lubricant compositions comprising oils of lubricant viscosity or greases prepared therefrom. Partially oxidized derivatives, i.e., where one or more of the sulfide groups is oxidized, to a sulfoxide or sulfone of the above-described polyesters also possess good load-carrying characteristics.

2. Description of the Prior Art

It is known to use organic sulfur compounds as additives for lubricating oils. These compounds provide extreme pressure properties to lubricants, however, the presence of sulfur in lubricating oils can cause corrosion of metal parts in contact with the lubricant. Oil-insolubility of some organic sulfur compounds is an additional problem.

SUMMARY OF THE INVENTION

It has now been found that incorporation of the polyester moiety derived from the herein below disclosed polysulfideorganocarboxylic acids impart good load-carrying protection to lubricants and are readily oil soluble.

Accordingly, this invention is directed to polyesters of polysulfideorganocarboxylic acids having the following general formula:

where n is 1 to 8 and in which one or more sulfur atoms in the chain may be oxidized to sulfoxide (S=O) or sulfone

X and Y may be the same or different and are individually selected from H, alkyl, and cycloalkyl of from 1 to 10 carbon atoms and —CH$_2$CO$_2$R", R, R' and R" which may be the same or different and are individually selected from alkyl, alkenyl, cycloalkyl, aralkyl, and alkaryl of from 1 to 32 carbon atoms.

DESCRIPTION OF SPECIFIC EMBODIMENTS

The additives in accordance with this invention may be conveniently prepared as follows:

A mercaptoester is added dropwise to a stoichiometric mixture of sulfur and tert-butylamine in hexane. The reaction mixture is then refluxed for 2 to 6 hr., and cooled. After diluting with ether and washing with aqueous potassium carbonate and water, the organic portion is stripped of solvent to give the clear product. Although this is a preferred embodiment, it is understood that any alternative preparations known in the art may also be used.

The polysulfidepolyesters may then be partially oxidized to produce derivatives wherein one or more of the sulfide groups are oxidized to a sulfone or a sulfoxide. However, the oxidized derivative may also be prepared by reacting the mercaptoester with thionyl or sulfuryl chloride. Both the polysulfidepolyesters and their oxidized derivatives exhibit good load-carrying characteristics.

The controlled oxidation may be carried out in any convenient manner known to the art. Any standard oxidizing agent is suitable including n-chlorobenzotriazole.

The load-carrying additives described herein are effectively employed in standard conventional amounts, that is, from about 0.01 to about 5% by weight thereof based on the total weight of the composition. They are compatible with any other additives normally used in such compositions, such as for example antioxidants, viscosity control agents and detergents.

This application in its preferred embodiments is directed to lubricant compositions comprising a major amount, of an oil of lubricating viscosity, or grease prepared therefrom and a minor amount sufficient to improve the load-carrying properties of said lubricant compositions, of said polysulfides.

The subject polysulfides exhibit good load-carrying activity in mineral oils or fractions thereof, synthesized hydrocarbon base stocks, ester base stocks or mixed base stocks. The lubricant compositions hereof accordingly may comprise any materials that normally exhibit insufficient load-carrying properties. Especially suitable for use with the additives of this invention are liquid hydrocarbon oils boiling within the range from about 75° F. to about 1,000° F. Lubricant oils, improved in accordance with the present invention, may be of any suitable lubricating viscosity, ranging from about 45 SSU at 100° F. to about 6,000 SSU at 100° F. and, preferably, from about 50 to 250 SSU at 210° F. Oils having viscosity indexes from about 70 to about 95 at 210° F. are preferred. The average molecular weight of these oils ranges from about 250 to about 800. In general, the lubricant compositions may comprise any mineral or synthetic oil of lubricating viscosity.

In instances where synthetic oils are desired in preference to mineral oils they may be employed alone or in combination with a mineral oil. They may also be used as the vehicle or base for grease compositions. Typical synthetic lubricants include polyisobutylene, polybutenes, hydrogenated polydecenes, polypropylene glycol, polyethylene glycol, trimethylol propane esters, neopentyl and pentaerythritol esters, di(2-ethyl hexyl) sebacate, di(2-ethyl hexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis(p-phenoxy phenyl) ether, phenoxy phenylethers, dialkylbenzenes, etc.

As hereinbefore indicated, the aforementioned additives can be incorporated into grease compositions as antiwear agents. When high temperature stability is not a requirement of the finished grease, mineral oils having a viscosity of at least 40 SSU at 150° F., and particularly those falling within the range of from about 60 SSU to about 6,000 SSU at 100° F. may be employed. The lubricating compositions of the improved greases of the present invention, containing the above-described additives, are combined with a grease-forming quantity of a thickening agent. For this purpose, a wide variety of materials can be dispersed in the lubricating oil in grease-forming quantities in such degree as to impart to the resulting grease composition the desired consistency. Exemplary of the thickening agents that may be employed in the grease formulation are non-soap thickeners, such as surface-modified clays and silicas, aryl ureas, calcium complexes and similar materials. In general, grease thickeners are employed which do not melt or dissolve when used at the required temperature within a particular environment; however, in all other respects, any material which is normally employed for thickening or gelling oleaginous fluids or forming grease may be used in the present invention.

The following examples are intended to exemplify the herein embodied invention and are in no way intended to limit the scope thereof. Product identification was by standard elemental analysis techniques.

EXAMPLE 1

was prepared as follows:

Sublimed sulfur (19.2 g, 0.6 g atm.) and 500 ml of n-hexane, and 6 ml of tert-butylamine were charged into a one liter reaction flask (protected from moisture) and stirred. To this mixture were added 82 g (0.4 moles) of isooctyl mercaptoacetate, dropwise, at ambient temperature, under a slow stream of nitrogen. After the addition, the mixture was heated at 45°–55° C. for 3 hr., cooled, diluted with ether and washed with 5% $K_2CO_3$ and then water. The organic portion was dried over magnesium sulfate and stripped of solvent to give the clear product.

EXAMPLE 2

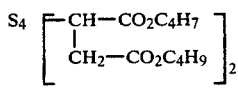

was prepared as in Example 1 except that dibutyl mercaptosuccinate was added (instead of isooctyl mercaptoacetate), and a clear amber colored product was obtained.

EXAMPLE 3

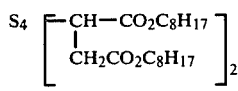

was prepared as follows:

Di-octyl mercaptosuccinate (40 g, 0.11 moles) were added to 100 ml of n-hexane and stirred. At ambient temperature and under a slow nitrogen purge, a solution of sulfur monochloride (7 g, 0.05 moles) in 20 ml of n-hexane was added dropwise to the reaction mixture, after which it was refluxed for 5 hr. The reaction mixture was diluted with ether and washed with 5% $K_2CO_3$ and the organic portion was separated and dried over $MgSO_4$ and stripped to give the product a light yellow liquid.

EXAMPLE 4

The compound of Example 3 prepared in the alternate manner indicated below:

Sublimed sulfur, 14 g (0.4 moles), 15 ml of tert-butylamine, and 500 ml of n-hexane were charged into a 2-liter reaction flask. While stirring under slight nitrogen purge, 120 g (0.3 moles) of di-octyl mercaptosuccinic acid were added dropwise. After refluxing for 2 hr., the reaction mixture was cooled, diluted with benzene and washed with 5% $Na_2CO_3$, water, and dried over $MgSO_4$. It was then stripped to give the desired product.

EXAMPLE 5

was prepared essentially as in Example 4, except that 19.2 (0.6 g atm.) of sulfur and 153 g (0.75 moles) of isooctyl thioacetate were used.

EXAMPLE 6

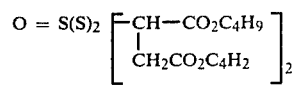

was prepared as follows:

Di-butyl mercaptosuccinate (0.1 moles) and 100 ml of n-hexane were charged into a 500 ml reaction flask and stirred. To this was added, at ambient temperature, a solution of 6 g (0.05 moles) of thionyl chloride in 10 ml of n-hexane dropwise under a slow nitrogen purge. The reaction mixture was heated at 45° C. for 3 hr., cooled and diluted with ether. It was then washed with a 5% solution of $K_2CO_3$, and the organic portion dried over $MgSO_4$ and stripped to give the product, a clear amber colored material.

EXAMPLE 7

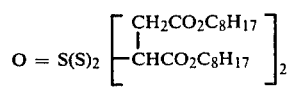

was prepared as in Example 6, except that di-octyl mercaptosuccinate (80 g, 0.21 moles) and 12 g (0.1 moles) of thionyl chloride were used.

EXAMPLE 8

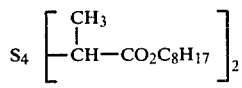

was prepared as in Example 4 except that 32.5 g (0.15 moles) of n-octyl-2-mercaptopropionate and 7 g (0.22 g atm) were used.

EXAMPLE 9

The compound of Example 8 prepared in the alternate manner detailed below:

n-octyl-2-mercaptopropionate, (44 g, 0.2 moles) and 100 ml of n-hexane were charged into a reaction flask protected from moisture. While stirring under a slow nitrogen purge, a solution of 12 g (0.08 moles) of sulfur monochloride was added dropwise to the mixture at ambient temperature. Following the moderately exothermic reaction, the reaction mixture was heated at 40°–50° C. for 5 hr., cooled, diluted with ether and washed with 5% $K_2CO_3$. The organic portion was further washed with water, dried over $MgSO_4$ and stripped to give a clear light yellow product.

The compounds of Examples 1 to 8 were then subjected to a standard Four Ball Wear Test using ½ inch 52110 steel balls at a load of 60 kg for 30 minutes. Other test conditions and the results thereof are contained in Table 1 below. The base stock used in the test was an 80/20 mixture of a solvent refined Mid-Continent paraffinic 150/160 second bright mineral oil and a 200/210 second refined Mid-Continent neutral mineral oil.

TABLE 1

| | | | | 4-Ball Wear Test - Scar Diameter (mm) | | | | |
|---|---|---|---|---|---|---|---|---|
| | | Conc. | Temp. | SPEED (RPM) | | | | |
| Ex. | Additive | Wt % | °F. | 500 | 1,000 | 1,500 | 2,000 | |
| | Mineral Oil | 100 | Room | 0.50 | 0.60 | 0.88 | 2.34 | |
| | Base Stock | | 200 | 0.60 | 1.06 | 1.86 | 2.23 | |
| | | | 390 | 1.00 | 1.31 | 2.06 | — | |
| 1 | $S_4(CH_2CO_2C_8H_{17})_2$ | 1 | Room | 0.50 | 0.65 | 0.80 | 0.85 | |
| | | | 200 | 0.50 | 0.65 | 0.80 | 0.95 | |
| | | | 390 | 1.0 | 0.90 | 0.90 | 0.95 | |
| 2 | $S_4\left[\begin{array}{c}-CH-CO_2C_4H_9\\|\\CH_2CO_2C_4H_9\end{array}\right]_2$ | 1 | Room | 0.40 | 0.60 | 0.70 | 0.85 | |
| | | | 200 | 0.50 | 0.60 | 0.80 | 0.90 | |
| | | | 390 | 0.80 | 0.85 | 0.95 | 1.0 | |
| 3 | $S_4\left[\begin{array}{c}-CH-CO_2C_8H_{17}\\|\\CH_2CO_2C_8H_{17}\end{array}\right]_2$ | 1 | Room | 0.50 | 0.50 | 0.70 | 1.0 | |
| | | | 200 | 0.50 | 0.60 | 0.80 | 0.95 | |
| | | | 390 | 0.70 | 0.80 | 0.90 | 1.05 | |
| 4 | (Ex. 3, alternative Prep.) | 1 | Room | 0.50 | 0.60 | 0.85 | 0.95 | |
| | | | 200 | 0.50 | 0.60 | 0.85 | 0.95 | |
| | | | 390 | 1.0 | 1.0 | 1.0 | 1.0 | |
| 5 | $S_3(CH_2CO_2C_8H_{17})_2$ | 1 | Room | 0.50 | 0.60 | 0.80 | 0.85 | |
| | | | 200 | 0.50 | 0.60 | 0.70 | 0.90 | |
| | | | 390 | 1.0 | 1.05 | — | — | |
| 6 | $O=S(S)_2\left[\begin{array}{c}-CH-CO_2C_4H_9\\|\\CH_2CO_2C_4H_9\end{array}\right]_2$ | 1 | Room | 0.40 | 0.55 | 0.70 | 0.90 | |
| | | | 200 | 0.45 | 0.55 | 0.85 | 1.0 | |
| | | | 390 | 0.60 | 0.70 | 1.05 | 1.0 | |
| 7 | $O=S(S)_2\left[\begin{array}{c}CH_2CO_2C_8H_{17}\\|\\-CHCO_2C_8H_{17}\end{array}\right]_2$ | 1 | Room | 0.45 | 0.60 | 0.70 | 0.85 | |
| | | | 200 | 0.50 | 0.70 | 0.80 | 2.0 | |
| | | | 390 | 0.90 | 0.80 | 1.50 | 2.0 | |
| 8 | $S_4\left[\begin{array}{c}CH_3\\|\\-CH-CO_2C_8H_{17}\end{array}\right]_2$ | 1 | Room | 0.40 | 0.50 | 1.90 | 2.0 | |
| | | | 200 | 0.40 | 0.50 | 0.80 | 0.80 | |
| | | | 390 | 0.90 | 1.40 | 2.0 | 2.0 | |
| 9 | (Ex. 8, alternative Prep.) | 1 | Room | 0.50 | 0.55 | 0.75 | 1.0 | |
| | | | 200 | 0.50 | 0.65 | 0.80 | 0.90 | |
| | | | 390 | 0.80 | 1.45 | — | — | |

Table 2 shows the evaluative data obtained from testing a representative additive compound in accordance with the invention (Example 2) in an ester base stock made by reacting pentaerythritol with an equimolar mixture of $C_5$ and $C_9$ monocarbocylic acids.

TABLE 2

| | | | | 4-Ball Wear Test Scar Diameter | | | |
|---|---|---|---|---|---|---|---|
| | | Conc. | Temp. | SPEED (RPM) | | | |
| Ex. | Additive | Wt % | °F. | 500 | 1,000 | 1,500 | 2,000 |
| 1 | None (Base Stock Ester Fluid) | 100 | Room | 0.70 | 0.90 | 0.90 | 1.95 |
| | | | 200 | 0.80 | 0.90 | 2.00 | 2.10 |
| | | | 390 | 0.90 | 1.30 | — | 2.40 |
| 2 | $S_4\left[\begin{array}{c}-CH-CO_2C_8H_{17}\\|\\CH_2-CO_2C_8H_{17}\end{array}\right]_2$ | | Room | 0.75 | 0.80 | 1.10 | 1.00 |
| | | | 200 | 0.73 | 0.80 | 1.16 | 1.15 |
| | | | 390 | 0.75 | 1.05 | 1.60 | 1.40 |

The data of Tables 1 and 2 clearly show that the herein disclosed compounds are excellent load-carrying additives in both mineral and synthetic lubricants.

The description and disclosure of the preferred embodiments of this invention are not to be construed as limitations of the invention.

I claim:

1. A compound having the following general formula:

$$[RO_2CCXY]S_n[CXYCO_2R']$$

where n is 1 to 8 and in which one or more sulfur atoms in the chain are oxidized to sulfoxide (S=O) or sulfone

X and Y may be the same or different and are individually selected from H, alkyl, and cycloalkyl of from 1 to 10 carbon atoms and —$CH_2CO_2R''$; R, R' and R'' may be the same or different and are individually selected from alkyl, alkenyl, cycloalkyl, aralkyl, and alkaryl of from 1 to 32 carbon atoms.

2. The compound of claim 1 having the following formula:

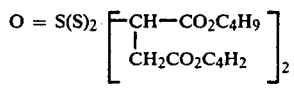

3. The compound of claim 1 having the following formula:

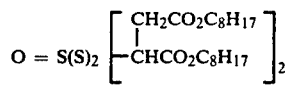

4. A lubricant composition comprising a major amount of an oil of lubricating viscosity or grease prepared therefrom and a minor effective load-carrying amount of a compound having the following general formula:

[RO$_2$CCXY]S$_n$[CXYCO$_2$R']

where n is 1 to 8 and in which one or more sulfur atoms in the chain are oxidized to sulfoxide (S=O) or sulfone

X and Y may be the same or different and are individually selected from H, alkyl, and cycloalkyl of from 1 to 10 carbon atoms, and —CH$_2$CO$_2$R" where R, R' and R" may be the same or different and are individually selected from alkyl, alkenyl, cycloalkyl, aralkyl and alkaryl of from 1 to 32 carbon atoms.

5. The lubricant composition of claim 4 comprising a major amount of an oil of lubricating viscosity or grease prepared therefrom and a minor effective load-carrying amount of a compound having the following formula:

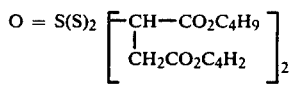

6. The lubricant composition of claim 4 comprising a major amount of an oil of lubricating viscosity or grease prepared therefrom and a minor effective load-carrying amount of a compound having the following formula:

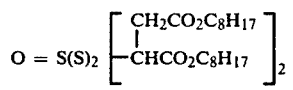

7. The lubriant composition of claim 4 wherein said minor effective load-carrying amount of said compound is from about 0.01 to 5 wt. % based on the total weight of the composition.

* * * * *